(12) United States Patent
Kotanko et al.

(10) Patent No.: US 12,076,472 B2
(45) Date of Patent: Sep. 3, 2024

(54) SYSTEMS AND METHODS FOR MONITORING FLUID VOLUMES DURING PERITONEAL DIALYSIS

(71) Applicant: FRESENIUS MEDICAL CARE HOLDINGS, INC., Waltham, MA (US)

(72) Inventors: Peter Kotanko, New York, NY (US); Fansan Zhu, Flushing, NY (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 643 days.

(21) Appl. No.: 17/066,554

(22) Filed: Oct. 9, 2020

(65) Prior Publication Data
US 2021/0106741 A1   Apr. 15, 2021

Related U.S. Application Data

(60) Provisional application No. 62/913,217, filed on Oct. 10, 2019.

(51) Int. Cl.
*A61M 1/28* (2006.01)
*G16H 20/17* (2018.01)
(Continued)

(52) U.S. Cl.
CPC ............ *A61M 1/282* (2014.02); *G16H 20/17* (2018.01); *G16H 20/40* (2018.01); *G16H 40/63* (2018.01); *A61B 5/03* (2013.01); *A61M 2205/18* (2013.01); *A61M 2205/3331* (2013.01); *A61M 2205/3368* (2013.01); *A61M 2205/52* (2013.01); *A61M 2209/088* (2013.01); *A61M 2210/1017* (2013.01); *A61M 2210/1021* (2013.01); *A61M 2230/65* (2013.01)

(58) Field of Classification Search
None
See application file for complete search history.

(56) References Cited

U.S. PATENT DOCUMENTS

| 5,643,201 A * | 7/1997 | Peabody | A61M 1/1643 |
| | | | 604/29 |
| 7,228,170 B2 * | 6/2007 | Zhu | A61B 5/4869 |
| | | | 600/547 |
| 7,354,417 B1 * | 4/2008 | Levin | A61M 1/284 |
| | | | 604/29 |

(Continued)

FOREIGN PATENT DOCUMENTS

CN        104411242 A *  3/2015   ........... A61B 5/1451

OTHER PUBLICATIONS

English Translation for CN 104411242 A (Year: 2015).*
(Continued)

*Primary Examiner* — Jenna Zhang
(74) *Attorney, Agent, or Firm* — Lando & Anastasi, LLP

(57) ABSTRACT

Techniques for monitoring fluid volumes during peritoneal analysis include: computing lower abdominal fluid volumes, continuously during a dwell time of a peritoneal dialysis treatment, based at least on bioimpedance data from electrodes positioned on a patient's upper thighs; and computing intraperitoneal volumes, continuously during the dwell time of the peritoneal dialysis treatment, based at least on bioimpedance data from the electrodes positioned on the patient's upper thighs and electrodes positioned on the patient's torso.

10 Claims, 12 Drawing Sheets

(51) Int. Cl.
   *G16H 20/40*   (2018.01)
   *G16H 40/63*   (2018.01)
   *A61B 5/03*   (2006.01)

(56) References Cited

U.S. PATENT DOCUMENTS

| | | | |
|---|---|---|---|
| 2006/0241543 A1* | 10/2006 | Gura | A61M 1/3639 |
| | | | 604/5.01 |
| 2013/0211322 A1* | 8/2013 | Degen | A61M 1/285 |
| | | | 604/29 |
| 2014/0066841 A1 | 3/2014 | Degen et al. | |
| 2015/0133854 A1* | 5/2015 | Zhu | A61B 5/1451 |
| | | | 604/28 |

OTHER PUBLICATIONS

International Search Report and Written Opinion from corresponding International Application No. PCT/US2020/054910 dated Feb. 10, 2021.

Heimburger et al., "A quantitative description of solute and fluid transport during peritoneal dialysis", Kidney International, 1992, vol. 41, pp. 1320-1332.

Mehrotra et al., "The Current State of Peritoneal Dialysis", J Am Soc Nephrol, 2016, vol. 27, pp. 3238-3252.

Zhu et al., "Measurement of intraperitoneal volume by segmental bioimpedance analysis during peritoneal dialysis", American Journal of Kidney Diseases, 2003, vol. 42, pp. 167-172.

* cited by examiner

SYSTEMS AND METHODS FOR MONITORING FLUID VOLUMES DURING PERITONEAL DIALYSIS

RELATED APPLICATIONS

This application claims the benefit of U.S. Provisional Patent Application Ser. No. 62/913,217, titled "Systems and Methods for Monitoring Fluid Volumes During Peritoneal Dialysis," filed Oct. 10, 2019, which is hereby incorporated by reference in its entirety.

BACKGROUND

Peritoneal dialysis is a renal replacement therapy for patients who suffer from renal disease. In clinical practice, it is difficult to obtain information about changes in the fluid volume in the peritoneal cavity during the dwell time. To understand the characteristics of the peritoneal membrane, knowledge of the ultrafiltration volume (UFV) is important in clinical routine. For a single peritoneal dialysis treatment, the final ultrafiltration volume may be computed based on the difference in weight between the drained dialysate and the infused dialysate. However, the difference in weight between the drained dialysate and the infused dialysate does not provide any knowledge of the dynamic changes of intraperitoneal volume (IPV) during the dwell time, including the timing of peak intraperitoneal volume.

Approaches described in this section have not necessarily been conceived and/or pursued prior to the filing of this application. Accordingly, unless otherwise indicated, approaches described in this section should not be construed as prior art.

SUMMARY

One or more embodiments include a device and method for continuously monitoring changes in fluid in a patient's lower abdomen and/or peritoneal cavity. The device may be fixed with a belt or other wearable item, e.g., around the patient's waist.

One or more embodiments include a pressure sensor that is used to monitor pressure of dialysate in the peritoneal cavity during dwell time. The device may compute one or more metrics based on the pressure data. For example, the device may compute tissue compliance as a function of changes in pressure and changes in fluid volume.

One or more embodiments include a temperature sensor that is used to monitor temperature of dialysate in the peritoneal cavity during dwell time. The device may compute one or more metrics based on the temperature data.

One or more embodiments use multifrequency bioimpedance, in which 4 to 8 electrodes are used to inject current and measure fluid changes. The electrodes may be made of any conductive material. Some of all of the electrodes may be integrated into a garment (e.g., underwear, a belt, and/or another type of garment) worn by the patient.

One or more embodiments transmit some or all of the signals to and/or from the device using wireless networking techniques.

One or more embodiments include one or more switches (e.g., a three-way switch) to control dialysate infusion, dwell time, and draining. The device may transmit instructions to a peritoneal dialysis device to control the switch(es) and/or to control one or more other components of a peritoneal dialysis device.

One or more embodiments use bioimpedance data to detect maximal fluid volume in the peritoneal cavity.

One or more embodiments include one or more body composition models that allow for measurement of intraperitoneal fluid volume and/or lower abdominal fluid volume (e.g., interstitial fluid volume and/or urinary bladder volume). A body composition model may be an equivalent electrical circuit model that describes lower abdominal body composition and/or peritoneal cavity composition with resistances. The equivalent electrical circuit model may also include one or more capacitances.

One or more embodiments allow for measurement of fluid in both the peritoneal cavity and the lower abdomen (e.g., interstitial tissue and/or urinary bladder), separately or simultaneously. The device may be configured to switch between computation modes, e.g., under control of a digital switch.

One or more embodiments may be applied to monitoring changes in fluid at other locations in the body. For example, a device and/or method described herein may be used to continuously monitor accumulating fluid in the abdomen due to liver disease, pleural effusion due to heart disease, and/or internal bleeding for a variety of reasons.

In general, in one aspect, a device includes one or more processors and one or more non-transitory computer-readable media storing instructions that, when executed by the one or more processors, cause the device to perform operations including: computing lower abdominal fluid volumes, continuously during a dwell time of a peritoneal dialysis treatment, based at least on bioimpedance data from electrodes positioned on a patient's upper thighs; and computing intraperitoneal volumes, continuously during the dwell time of the peritoneal dialysis treatment, based at least on bioimpedance data from the electrodes positioned on the patient's upper thighs and electrodes positioned on the patient's torso.

The operations may further include: detecting a first switching condition for switching from a first computation mode for computing the plurality of lower abdominal fluid volumes to a second computation mode for computing the intraperitoneal volumes; and responsive to detecting the first switching condition, switching from the first computation mode to the second computation mode. The operations may further include: detecting a second switching condition for switching from the second computation mode to the first computation mode; and responsive to detecting the second switching condition, switching from the second computation mode to the first computation mode. The first switching condition and the second switching condition may be states of a digital switch.

The operations may further include: detecting a first switching condition for switching from a first computation mode for computing the intraperitoneal volumes to a second computation mode for computing the lower abdominal fluid volumes; and responsive to detecting the first switching condition, switching from the first computation mode to the second computation mode. The operations may further include detecting a second switching condition for switching from the second computation mode to the first computation mode; and responsive to detecting the second switching condition, switching from the second computation mode to the first computation mode. The first switching condition and the second switching condition may be states of a digital switch.

The operations may further include obtaining bioimpedance data from the first plurality of electrodes and the second plurality of electrodes via wireless transmissions.

Computing the lower abdominal fluid volumes may include applying bioimpedance data from the electrodes positioned on the patient's upper thighs to an electrical circuit model that is based at least in part on interstitial tissue resistance and peritoneal cavity resistance. The electrical circuit model may include at least interstitial tissue resistance, peritoneal cavity resistance, local muscle resistance, and urinary bladder resistance in parallel, wherein the electrical circuit model can be simplified as interstitial tissue resistance and peritoneal cavity resistance in parallel, and wherein interstitial tissue resistance is greater than peritoneal cavity resistance, such that the electrical model can be used to compute changes in lower abdominal fluid volume.

Computing the peritoneal volumes may include applying bioimpedance data from the electrodes positioned on the patient's upper thighs to an electrical circuit model that is based at least in part on (a) a first resistance between a first electrode in the first plurality of electrodes and a second electrode in the second plurality of electrodes in parallel with (b) a second resistance between a third electrode in the first plurality of electrodes and a fourth electrode in the second plurality of electrodes. The first resistance may correspond to peritoneal cavity resistance on a right side of the patient's body and the second resistance may correspond to peritoneal cavity resistance on a left side of the patient's body.

The electrodes positioned on the patient's upper thighs may include a first pair of electrodes in close proximity on the patient's upper right thigh and a second pair of electrodes in close proximity on the patient's upper left thigh, and the electrodes positioned on the patient's torso may include a third pair of electrodes in close proximity on the patient's right torso and a fourth pair of electrodes in close proximity on the patient's left torso.

The operations may further include transmitting an instruction to control operation of a peritoneal dialysis device, based at least on one or more of the lower abdominal fluid volumes and/or the intraperitoneal volumes.

The electrodes positioned on the patient's upper thighs may be integrated into a garment worn by the patient. The lower abdominal fluid volumes may correspond to bladder volumes. The lower abdominal fluid volumes may correspond to interstitial volumes.

In general, in one aspect, a device includes one or more processors and one or more non-transitory computer-readable media storing instructions that, when executed by the one or more processors, cause the device to perform operations including: computing intraperitoneal volumes, continuously during a dwell time of a peritoneal dialysis treatment, based at least on bioimpedance data from (a) electrodes positioned on a patient's upper thighs and (b) electrodes positioned on the patient's torso; obtaining pressures of dialysate, continuously during the dwell time, in the patient's peritoneal cavity; and computing tissue compliance values, continuously during the dwell time, based at least on the intraperitoneal volumes and the pressures of dialysate in the patient's peritoneal cavity.

The operations may further include: determining that at least one tissue compliance value in the tissue compliance values corresponds to a pathological condition; and generating an alert indicating detection of the pathological condition.

The operations may further include transmitting an instruction to control operation of a peritoneal dialysis device, based at least on at least one tissue compliance value in the tissue compliance values.

The operations may further include obtaining a temperatures of dialysate in the patient's peritoneal cavity, continuously during the dwell time.

The electrodes positioned on the patient's upper thighs may include a first pair of electrodes in close proximity on the patient's upper right thigh and a second pair of electrodes in close proximity on the patient's upper left thigh, and the electrodes positioned on the patient's torso may include a third pair of electrodes in close proximity on the patient's right torso and a fourth pair of electrodes in close proximity on the patient's left torso.

In general, in one aspect, a system includes electrodes configured for placement on a patient's upper thighs, electrodes configured for placement on the patient's torso, a device including one or more processors, and one or more non-transitory computer-readable media storing instructions that, when executed by the one or more processors, cause the device to perform operations including: computing lower abdominal fluid volumes, continuously during a dwell time of a peritoneal dialysis treatment, based at least on bioimpedance data from electrodes positioned on a patient's upper thighs; and computing intraperitoneal volumes, continuously during the dwell time of the peritoneal dialysis treatment, based at least on bioimpedance data from the electrodes positioned on the patient's upper thighs and electrodes positioned on the patient's torso.

The operations may further include: detecting a first switching condition for switching from a first computation mode for computing the plurality of lower abdominal fluid volumes to a second computation mode for computing the intraperitoneal volumes; and responsive to detecting the first switching condition, switching from the first computation mode to the second computation mode. The operations may further include: detecting a second switching condition for switching from the second computation mode to the first computation mode; and responsive to detecting the second switching condition, switching from the second computation mode to the first computation mode. The first switching condition and the second switching condition may be states of a digital switch.

The operations may further include: detecting a first switching condition for switching from a first computation mode for computing the intraperitoneal volumes to a second computation mode for computing the lower abdominal fluid volumes; and responsive to detecting the first switching condition, switching from the first computation mode to the second computation mode. The operations may further include detecting a second switching condition for switching from the second computation mode to the first computation mode; and responsive to detecting the second switching condition, switching from the second computation mode to the first computation mode. The first switching condition and the second switching condition may be states of a digital switch.

The operations may further include obtaining bioimpedance data from the first plurality of electrodes and the second plurality of electrodes via wireless transmissions.

Computing the lower abdominal fluid volumes may include applying bioimpedance data from the electrodes positioned on the patient's upper thighs to an electrical circuit model that is based at least in part on interstitial tissue resistance and peritoneal cavity resistance. The electrical circuit model may include at least interstitial tissue resistance, peritoneal cavity resistance, local muscle resistance, and urinary bladder resistance in parallel, wherein the electrical circuit model can be simplified as interstitial tissue resistance and peritoneal cavity resistance in parallel, and wherein interstitial tissue resistance is greater than peritoneal cavity resistance, such that the electrical model can be used to compute changes in lower abdominal fluid volume.

Computing the peritoneal volumes may include applying bioimpedance data from the electrodes positioned on the patient's upper thighs to an electrical circuit model that is based at least in part on (a) a first resistance between a first electrode in the first plurality of electrodes and a second electrode in the second plurality of electrodes in parallel with (b) a second resistance between a third electrode in the first plurality of electrodes and a fourth electrode in the second plurality of electrodes. The first resistance may correspond to peritoneal cavity resistance on a right side of the patient's body and the second resistance may correspond to peritoneal cavity resistance on a left side of the patient's body.

The electrodes positioned on the patient's upper thighs may include a first pair of electrodes in close proximity on the patient's upper right thigh and a second pair of electrodes in close proximity on the patient's upper left thigh, and the electrodes positioned on the patient's torso may include a third pair of electrodes in close proximity on the patient's right torso and a fourth pair of electrodes in close proximity on the patient's left torso.

The operations may further include transmitting an instruction to control operation of a peritoneal dialysis device, based at least on one or more of the lower abdominal fluid volumes and/or the intraperitoneal volumes.

The electrodes positioned on the patient's upper thighs may be integrated into a garment worn by the patient. The lower abdominal fluid volumes may correspond to bladder volumes. The lower abdominal fluid volumes may correspond to interstitial volumes.

In general, in one aspect, a system includes electrodes configured for placement on a patient's upper thighs, electrodes configured for placement on the patient's torso, a device including one or more processors, and one or more non-transitory computer-readable media storing instructions that, when executed by the one or more processors, cause the device to perform operations including: computing intraperitoneal volumes, continuously during a dwell time of a peritoneal dialysis treatment, based at least on bioimpedance data from (a) electrodes positioned on a patient's upper thighs and (b) electrodes positioned on the patient's torso; obtaining pressures of dialysate, continuously during the dwell time, in the patient's peritoneal cavity; and computing tissue compliance values, continuously during the dwell time, based at least on the intraperitoneal volumes and the pressures of dialysate in the patient's peritoneal cavity.

The operations may further include: determining that at least one tissue compliance value in the tissue compliance values corresponds to a pathological condition; and generating an alert indicating detection of the pathological condition.

The operations may further include transmitting an instruction to control operation of a peritoneal dialysis device, based at least on at least one tissue compliance value in the tissue compliance values.

The operations may further include obtaining a temperatures of dialysate in the patient's peritoneal cavity, continuously during the dwell time.

The electrodes positioned on the patient's upper thighs may include a first pair of electrodes in close proximity on the patient's upper right thigh and a second pair of electrodes in close proximity on the patient's upper left thigh, and the electrodes positioned on the patient's torso may include a third pair of electrodes in close proximity on the patient's right torso and a fourth pair of electrodes in close proximity on the patient's left torso.

In general, in one aspect, one or more non-transitory computer-readable media store instructions that, when executed by one or more processors, cause the one or more processors to perform operations including: computing lower abdominal fluid volumes, continuously during a dwell time of a peritoneal dialysis treatment, based at least on bioimpedance data from electrodes positioned on a patient's upper thighs; and computing intraperitoneal volumes, continuously during the dwell time of the peritoneal dialysis treatment, based at least on bioimpedance data from the electrodes positioned on the patient's upper thighs and electrodes positioned on the patient's torso.

The operations may further include: detecting a first switching condition for switching from a first computation mode for computing the plurality of lower abdominal fluid volumes to a second computation mode for computing the intraperitoneal volumes; and responsive to detecting the first switching condition, switching from the first computation mode to the second computation mode. The operations may further include: detecting a second switching condition for switching from the second computation mode to the first computation mode; and responsive to detecting the second switching condition, switching from the second computation mode to the first computation mode. The first switching condition and the second switching condition may be states of a digital switch.

The operations may further include: detecting a first switching condition for switching from a first computation mode for computing the intraperitoneal volumes to a second computation mode for computing the lower abdominal fluid volumes; and responsive to detecting the first switching condition, switching from the first computation mode to the second computation mode. The operations may further include detecting a second switching condition for switching from the second computation mode to the first computation mode; and responsive to detecting the second switching condition, switching from the second computation mode to the first computation mode. The first switching condition and the second switching condition may be states of a digital switch.

The operations may further include obtaining bioimpedance data from the first plurality of electrodes and the second plurality of electrodes via wireless transmissions.

Computing the lower abdominal fluid volumes may include applying bioimpedance data from the electrodes positioned on the patient's upper thighs to an electrical circuit model that is based at least in part on interstitial tissue resistance and peritoneal cavity resistance. The electrical circuit model may include at least interstitial tissue resistance, peritoneal cavity resistance, local muscle resistance, and urinary bladder resistance in parallel, wherein the electrical circuit model can be simplified as interstitial tissue resistance and peritoneal cavity resistance in parallel, and wherein interstitial tissue resistance is greater than peritoneal cavity resistance, such that the electrical model can be used to compute changes in lower abdominal fluid volume.

Computing the peritoneal volumes may include applying bioimpedance data from the electrodes positioned on the patient's upper thighs to an electrical circuit model that is based at least in part on (a) a first resistance between a first electrode in the first plurality of electrodes and a second electrode in the second plurality of electrodes in parallel with (b) a second resistance between a third electrode in the first plurality of electrodes and a fourth electrode in the second plurality of electrodes. The first resistance may correspond to peritoneal cavity resistance on a right side of the patient's body and the second resistance may correspond to peritoneal cavity resistance on a left side of the patient's body.

The electrodes positioned on the patient's upper thighs may include a first pair of electrodes in close proximity on the patient's upper right thigh and a second pair of electrodes in close proximity on the patient's upper left thigh, and the electrodes positioned on the patient's torso may include a third pair of electrodes in close proximity on the patient's right torso and a fourth pair of electrodes in close proximity on the patient's left torso.

The operations may further include transmitting an instruction to control operation of a peritoneal dialysis device, based at least on one or more of the lower abdominal fluid volumes and/or the intraperitoneal volumes.

The electrodes positioned on the patient's upper thighs may be integrated into a garment worn by the patient. The lower abdominal fluid volumes may correspond to bladder volumes. The lower abdominal fluid volumes may correspond to interstitial volumes.

In general, in one aspect, one or more non-transitory computer-readable media store instructions that, when executed by one or more processors, cause the one or more processors to perform operations including: computing intraperitoneal volumes, continuously during a dwell time of a peritoneal dialysis treatment, based at least on bioimpedance data from (a) electrodes positioned on a patient's upper thighs and (b) electrodes positioned on the patient's torso; obtaining pressures of dialysate, continuously during the dwell time, in the patient's peritoneal cavity; and computing tissue compliance values, continuously during the dwell time, based at least on the intraperitoneal volumes and the pressures of dialysate in the patient's peritoneal cavity.

The operations may further include: determining that at least one tissue compliance value in the tissue compliance values corresponds to a pathological condition; and generating an alert indicating detection of the pathological condition.

The operations may further include transmitting an instruction to control operation of a peritoneal dialysis device, based at least on at least one tissue compliance value in the tissue compliance values.

The operations may further include obtaining a temperatures of dialysate in the patient's peritoneal cavity, continuously during the dwell time.

The electrodes positioned on the patient's upper thighs may include a first pair of electrodes in close proximity on the patient's upper right thigh and a second pair of electrodes in close proximity on the patient's upper left thigh, and the electrodes positioned on the patient's torso may include a third pair of electrodes in close proximity on the patient's right torso and a fourth pair of electrodes in close proximity on the patient's left torso.

In general, in one aspect, one or more non-transitory computer-readable media store instructions that, when executed by one or more processors, cause the one or more processors to perform operations including: controlling one or more switches to enable communication with a first subset of electrodes positioned on a peritoneal dialysis patient; computing an intraperitoneal volume, based at least on first bioimpedance data from the first subset of electrodes; controlling the one or more switches to enable communication with a second subset of the electrodes positioned on the peritoneal dialysis patient, at least one electrode in the first subset being different from any electrode in the second subset; and computing an extraperitoneal volume, based at least on second bioimpedance data from the second subset of electrodes. The one or more switches may control relay boxes each associated with one or more respective electrodes.

The operations may further include adjusting one or more of a sample rate or interval of measurement between intraperitoneal volume and extraperitoneal volume.

One or more embodiments described in this Specification and/or recited in the claims may not be included in this General Overview section.

BRIEF DESCRIPTION OF THE DRAWINGS

Various aspects of at least one embodiment are discussed below with reference to the accompanying Figures, which are not intended to be drawn to scale. The Figures are included to provide illustration and a further understanding of the various aspects and embodiments, and are incorporated in and constitute a part of this specification, but are not intended to define the limits of the disclosure. In the Figures, each identical or nearly identical component that is illustrated in various Figures is represented by a like numeral. For the purposes of clarity, some components may not be labeled in every figure. In the Figures.

DETAILED DESCRIPTION

Figure 1:
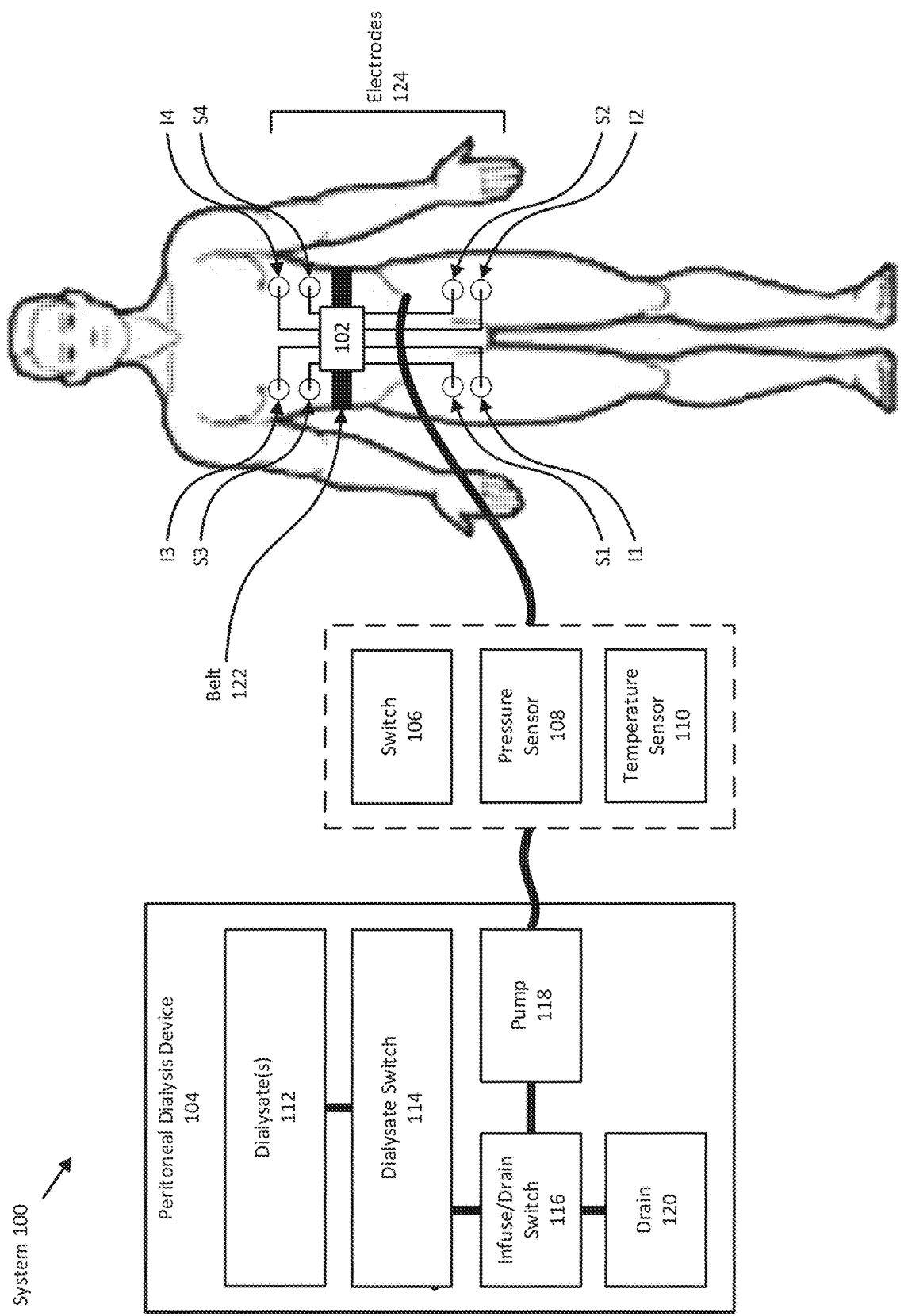
FIG. 1 is a block diagram of an example of a system according to an embodiment.

The following table of contents is provided for the reader's convenience and is not intended to define the limits of the disclosure.
1. SYSTEM ARCHITECTURE
2. ILLUSTRATIVE EXAMPLES
3. FLOW DIAGRAM
4. MISCELLANEOUS; EXTENSIONS
5. COMPUTING DEVICES 1. System Architecture FIG. 1 is a block diagram of an example of a system 100 according to an embodiment. In an embodiment, the system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

In an embodiment, a monitoring device 102 is fastened to a patient, for example on a belt 122 fixed on the patient's waist, a band, a clip, or other fastening device. Monitoring device 102 refers to hardware and/or software configured to perform operations described herein for monitoring fluid volumes during peritoneal dialysis. Examples of operations for monitoring fluid volumes during peritoneal dialysis are described below. Monitoring device 102 may include components described below with respect to FIG. 2.

In an embodiment, monitoring device 102 includes a wireless networking device (not shown), e.g., a wi-fi, Bluetooth®, and/or other type of wireless networking device, configured to receive data from one or more other components of system 100 (e.g., electrodes 124, pressure sensor 108, and/or temperature sensor 110) and/or transmit data to one or more other components of system 100 (e.g., switch 106, infuse/drain switch 116, and/or dialysate switch 114). One or more of the switches and/or switches described herein (including switches and/or switching conditions that may not be illustrated in FIG. 1) may be a digital switch, i.e., a switch that operates wholly or at least partially based on electrical signals and/or software instructions. One or more other components of system 100 may also include a wireless networking device (not shown) configured to communicate with monitoring device 102.

In an embodiment, to monitor fluid volumes, monitoring device 102 receives data from electrodes 124 placed on the patient's body. The electrodes 124 may be placed at locations that improve signal-to-noise ratios relative to other possible electrode placements (e.g., in comparison to placements at a patient's arm, foot, and/or trunk that produce lower signal-to-noise ratios). For example, one set of electrodes may be placed on the patient's thighs and another set of electrodes may be placed on the patient's torso. Specifically, a pair of electrodes S1, I1 may be placed in close proximity to each other on the patient's right thigh, a pair of electrodes S2, I2 may be placed on close proximity to each other on the patient's left thigh, a pair of electrodes I3, S3 may be placed in close proximity to each other on the patient's right torso, and a pair of electrodes I4, S4 may be placed in close proximity to each other on the patient's left torso. In an embodiment, this configuration allows for monitoring fluid volumes while improving signal-to-noise ratios relative to other possible electrode placements.

In an embodiment, electrodes I1, I2, I3, and I4 are current-injecting electrodes. Electrodes I1, I2, I3, and I4 may be configured to inject multifrequency current (for example, from 1 kHz to 1000 kHz) at their respective sites. Electrodes S1, S2, S3, and S4 are sensors used to capture bioimpedance data, e.g., to measure voltages. In an embodiment, monitoring device 102 uses data from the electrodes 124 to compute fluid volumes continuously (i.e., on an ongoing basis and/or at particular intervals) during a peritoneal dialysis treatment. The monitoring device 102 may compute peritoneal fluid volumes using bioimpedance spectroscopy. Techniques for computing peritoneal fluid volumes based on bioimpedance spectroscopy data are described in commonly owned Patent Cooperation Treaty (PCT) Patent Application Serial No. WO2013185080A1, titled "System and method of monitoring and control of ultrafiltration volume during peritoneal dialysis using segmental bioimpedance," filed Jun. 7, 2013, the entire contents of which are incorporated herein by reference.

In an embodiment, monitoring device 102 is configured to communicate with a peritoneal dialysis device 104. Peritoneal dialysis device 104 refers to hardware and/or software configured to supply and drain dialysate(s) 112 during a peritoneal dialysis treatment, for example using a pump 118. For example, peritoneal dialysis device 104 may be one of a range of peritoneal dialysis devices supplied by Fresenius Medical Care or another manufacturer.

In an embodiment, peritoneal dialysis device 104 is configured to supply a single dialysate 112. Alternatively, peritoneal dialysis device 104 may be configured to supply multiple dialysates 112, depending on the state of a dialysate switch 114. For example, the dialysates 112 may include 1.5% dextrose, 2.5% dextrose, and 4.25% dextrose. Dialysate switch 114 may be an n-way (e.g., three-way) switch for selecting between the available dialysates 112. In an embodiment, monitoring device 102 is configured to transmit instructions (e.g., over a wire and/or using a wireless protocol) to change the state of dialysate switch 114 and thereby switch the specific dialysate 112 being supplied by peritoneal dialysis device 104.

In an embodiment, peritoneal dialysis device 104 includes an infuse/drain switch 116 that switches between infusion and draining. When infuse/drain switch 116 is in an infusion state, peritoneal dialysis device 104 infuses dialysate 112 into the patient. When infuse/drain switch 116 is in a drain state, peritoneal dialysis device 104 removes fluid from the patient to a drain 120. Monitoring device 102 may be configured to transmit instructions (e.g., over a wire and/or using a wireless protocol) to change the state of infuse/drain switch 116 and thereby switch peritoneal dialysis device 104 from infusion to draining and/or vice versa.

In an embodiment, a switch 106 determines whether fluid flows between peritoneal dialysis device 104 and the patient. If switch 106 is in a closed state, fluid may not flow between peritoneal dialysis device 104 and the patient, regardless of the state of infuse/drain switch 116. If switch 106 is in an open state, fluid may flow to or from the patient, depending on the state of infuse/drain switch 116. Monitoring device 102 may be configured to transmit instructions (e.g., over a wire and/or using a wireless protocol) to change the state of switch 106 and thereby control whether fluid is permitted to flow between peritoneal dialysis device 104 and the patient. In an embodiment, switch 106 is a three-way switch configured to switch between infusion, draining, and dwell time. Switch 106 may also be configured to control pump 118, for example by wireless communication. Switch 106 may be a component of peritoneal dialysis device 104 or separate from peritoneal dialysis device 104.

In an embodiment, pressure sensor 108 is configured to measure fluid pressures. Specifically, pressure sensor 108 may be configured to measure fluid pressure in the peritoneal cavity. Pressure sensor 108 may be a component of switch 106.

In an embodiment, temperature sensor 110 is configured to measure dialysate temperatures. For example, temperature sensor 110 may be fixed on a catheter. Intraperitoneal temperature may be representative of the body's core temperature, which is important for certain diagnoses (e.g., inflammation and/or infection).

In an embodiment, combinations of measurements of intraperitoneal volume, intraperitoneal pressure, and/or intraperitoneal temperature may provide comprehensive biological information relevant to the care of peritoneal dialysis patients.

In an embodiment, one or more components of the system 100 are implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware firewall, a hardware network address translator (NAT), a hardware load balancer, a mainframe, a television, a content receiver, a set-top box, a printer, a mobile handset, a smartphone, a personal digital assistant ("PDA"), a wireless receiver and/or transmitter, a base station, a communication management device, a router, a switch, a controller, an access point, and/or a client device.

Figure 2:
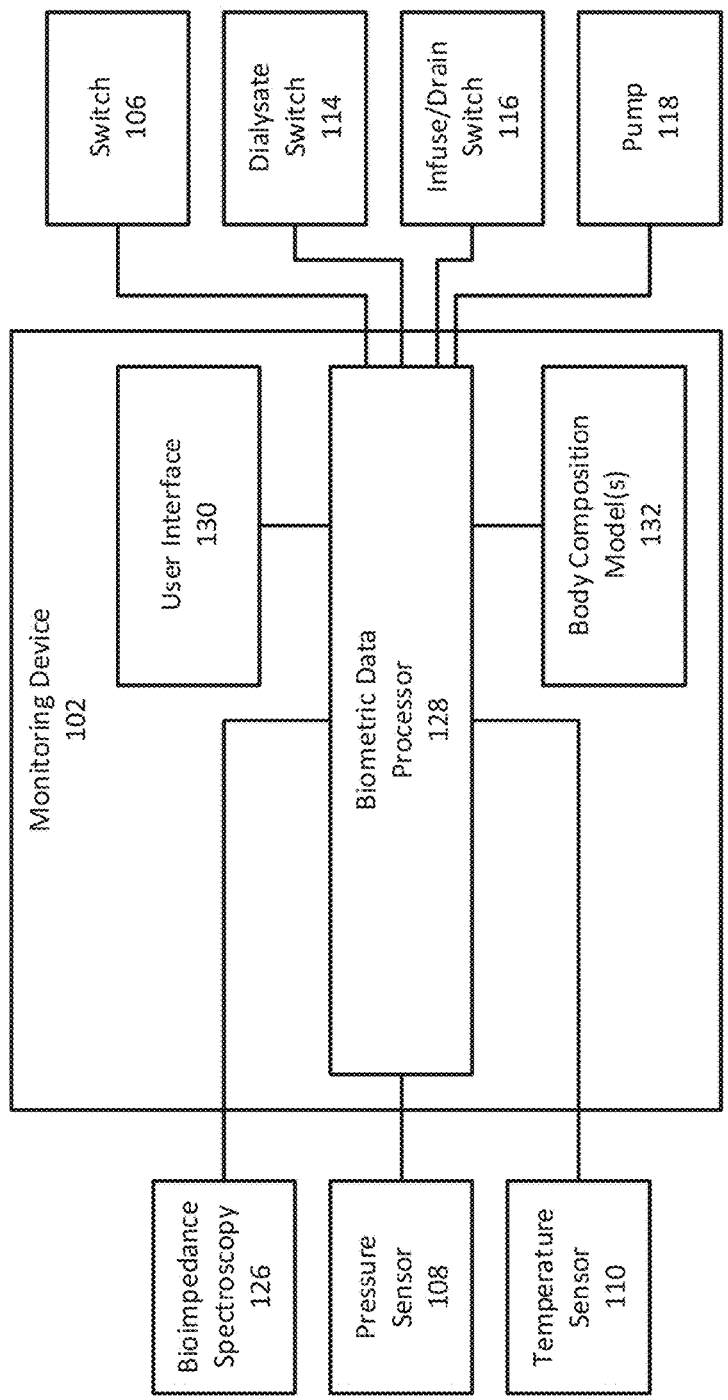
FIG. 2 is a block diagram of an example of a monitoring device according to an embodiment.

FIG. 2 is a block diagram of an example of a monitoring device 102 according to an embodiment. In an embodiment, the monitoring device 102 may include more or fewer components than the components illustrated in FIG. 2. The components illustrated in FIG. 2 may be local to or remote from each other. The components illustrated in FIG. 2 may be implemented in software and/or hardware. Each component may be distributed over multiple applications and/or machines. Multiple components may be combined into one application and/or machine. Operations described with respect to one component may instead be performed by another component.

In an embodiment, monitoring device 102 includes a biometric data processor 128. Biometric data processor 128 refers to hardware and/or software configured to receive signals from bioimpedance spectroscopy 126, pressure sensor 108, and/or temperature sensor 110, and generate output based on the signals. For example, biometric data processor 128 may include a signal processing component and a hardware processor configured to execute instructions. As discussed above, monitoring device 102 may be configured to receive one or more signals, corresponding to biometric data, wirelessly from the corresponding sensor(s). Specifically, bioimpedance spectroscopy 126 includes resistance data from electrodes 124 that reflects changes in fluid volumes. Biometric data processor 128 is configured to filter the input signals and analyze the input signals to compute fluid volumes. To compute fluid volumes, biometric data processor 128 may apply the input (or a transformation thereof) to one or more body composition model(s) 132. Body composition model(s) 132 may correspond to one or more equivalent electrical circuits. Examples of body composition model(s) 132 corresponding to equivalent electrical circuits are described below.

In an embodiment, in addition to fluid volumes, biometric data processor 128 is configured to compute one or more other metrics. For example, as described in further detail below, biometric data processor 128 may be configured to compute tissue compliance and/or other metrics that incorporate fluid temperature and/or fluid pressure.

In an embodiment, biometric data processor 128 is configured to generate output based on its computations. For example, biometric data processor 128 may be configured to transmit output to a user interface 130, transmit instructions to one or more switches (e.g., switch 106, dialysate switch 114, and/or infuse/drain switch 116), and/or transmit instructions to control a pump (e.g., pump 118). In an embodiment, biometric data processor 128 is configured to instruct peritoneal dialysis device 104 to switch between infusion, dwell time, and/or draining according to an algorithm designed to maximize ultrafiltration volume, e.g., according to a physician's prescription.

In an embodiment, a user interface 130 refers to hardware and/or software configured to facilitate communications between a user (e.g., a patient or clinician) and monitoring device 102. A user interface 130 renders user interface elements and receives input via user interface elements. A user interface 130 may be a graphical user interface (GUI), a command line interface (CLI), a haptic interface, a voice command interface, and/or any other kind of interface or combination thereof. Examples of user interface elements include checkboxes, radio buttons, dropdown lists, list boxes, buttons, toggles, text fields, date and time selectors, command lines, sliders, pages, and forms.

2. Illustrative Examples

Detailed examples are described below for purposes of clarity. Components and/or operations described below should be understood as examples that may not be applicable to one or more embodiments. Accordingly, components and/or operations described below should not be construed as limiting the scope of one or more embodiments.

Figure 3:
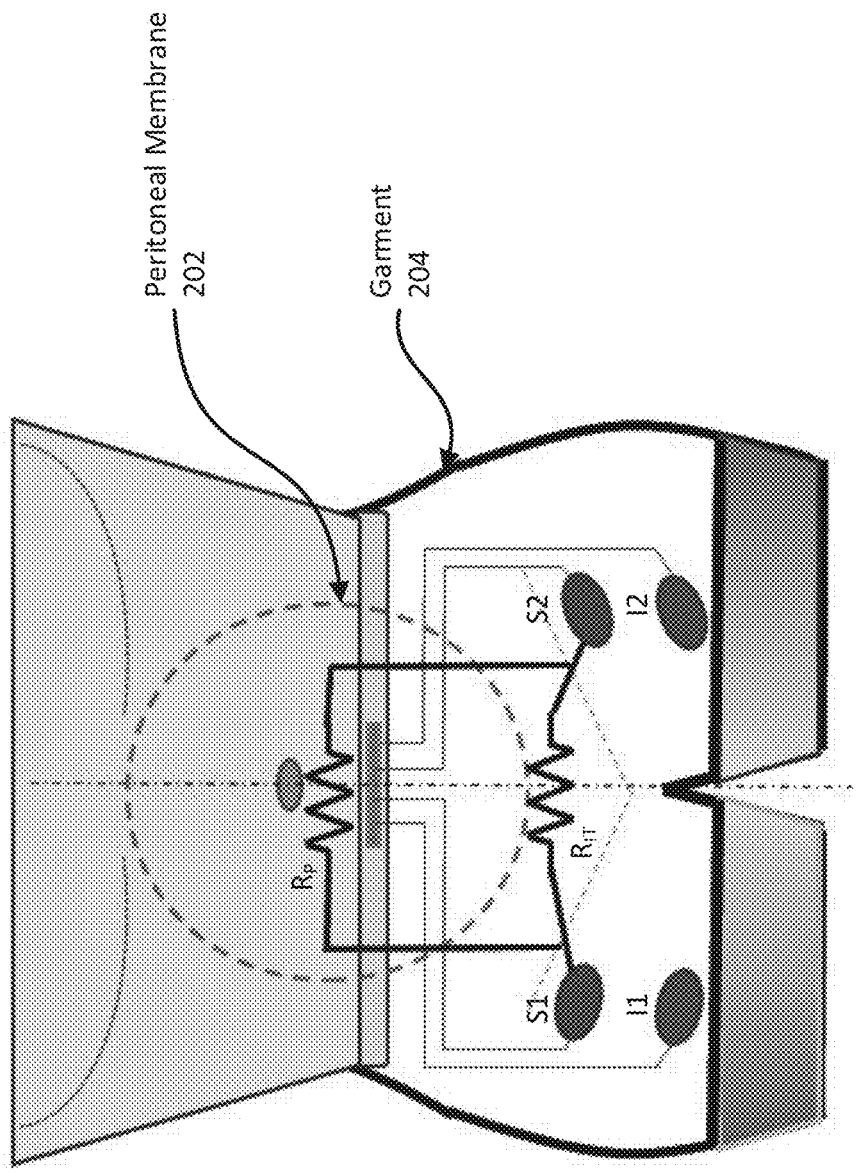
FIG. 3 illustrates an example of monitoring lower abdominal fluid volume according to an embodiment.

FIG. 3 illustrates an example of monitoring lower abdominal fluid volume according to an embodiment. As discussed above, electrodes I1 and I2 are current-injecting electrodes and electrodes S1 and S2 are sensors. $R_P$ and $R_{IT}$ represent resistances in the peritoneal cavity and interstitial tissue, respectively. The placement of electrodes shown in FIG. 3 may be used to measure changes in bioimpedance of interstitial space and in the bladder.

In addition, FIG. 3 illustrates an example of integrating electrodes I1, I2, S1, and S2 into a garment 204 worn by the patient, such as underwear or another type of garment. Other electrodes (e.g., electrodes I3, I4, S3, and S4) may also be integrated into the same garment 204 (with appropriate modifications, e.g., designing the garment 204 to also cover the patient's torso) and/or a separate garment. Integrating the electrodes into a garment 204 may help ensure proper placement of the electrodes to improve the signal-to-noise ratios and obtain more accurate bioimpedance spectroscopy.

Figure 4:
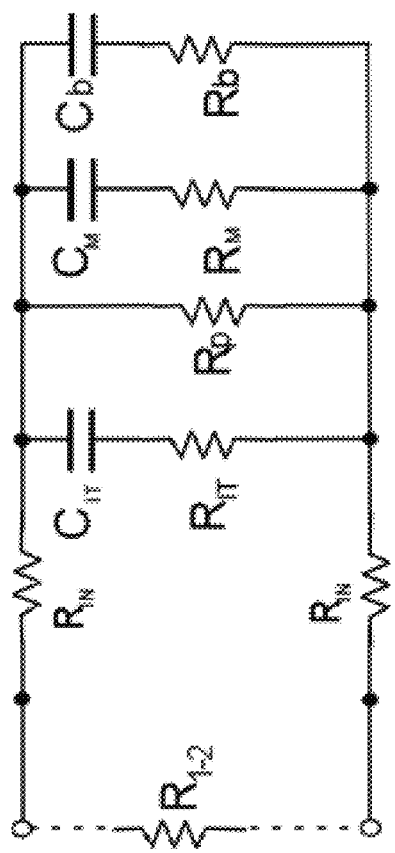
FIG. 4 illustrates an example of an electrical circuit model according to an embodiment.

FIG. 4 illustrates an example of an electrical circuit model according to an embodiment. Specifically, FIG. 4 illustrates an example of an equivalent electrical circuit model corresponding to the electrode placement of FIG. 3. This model describes lower abdominal body composition in which $R_{1-2}$ represents total resistance from electrodes S1 and S2. The two resistances $R_{IN}$ represent resistances between electrodes and skin, i.e., resistance from electrodes to abdominal compartment, which is less than the resistances in any of the compartments (including peritoneal cavity, muscle mass, bladder, and interstitial tissue). $R_M$ and $C_M$ represent local muscle resistance and capacitance, respectively. Rp represents resistance of the peritoneal cavity. $R_{IT}$ and $C_{IT}$ represent interstitial tissue resistance and capacitance, respectively. $R_b$ and $C_b$ represent resistance and capacitance of the urinary bladder, respectively. $R_{IT}$ is less than $R_P$ and $R_P$ is less than $R_M$. The model of FIG. 4 can be simplified as two resistances ($R_{IT}$ and $R_P$) in parallel connection. $R_b$ is constant in a peritoneal dialysis patient and may be ignored. Because the resistance Rp in the peritoneal cavity is larger than the resistance in interstitial tissue $R_{IT}$ or muscle $R_M$, the equivalent resistance from the model represents the resistance in interstitial tissue and/or the bladder. Therefore, the model of FIG. 4 may be used to compute changes in the volumes of interstitial tissue and/or bladder.

Figure 5:
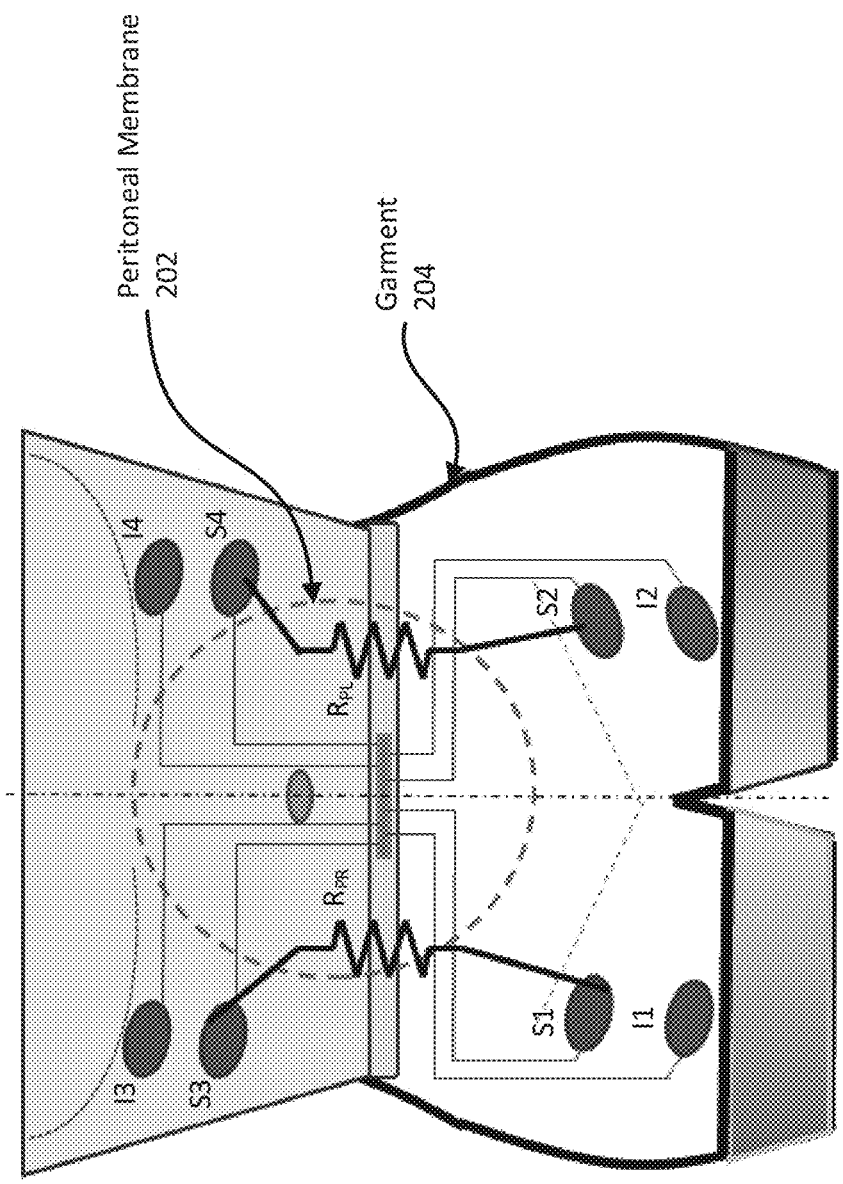
FIG. 5 illustrates an example of monitoring intraperitoneal volume according to an embodiment.

FIG. 5 illustrates an example of monitoring intraperitoneal volume according to an embodiment. Specifically, FIG. 5 illustrates placements of eight electrodes I1, S1, I2, S2, I3, S3, I4, S4 for measuring intraperitoneal volume. Two electrodes I1, I3 on the patient's right side and two electrodes I2, I4 on the patient's left side are used to inject current. Two electrodes S1, S3 on the patient's right side and two electrodes S2, S4 on the patient's left side are used to measure voltage producing the resistances $R_{PR}$ and $R_{PL}$ on the patient's right and left sides, respectively.

Figure 6:
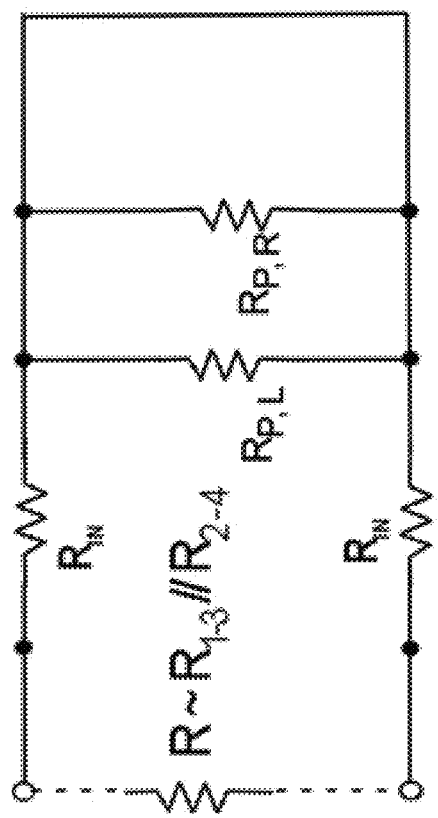
FIG. 6 illustrates an example of an electrical circuit model according to an embodiment.

FIG. 6 illustrates an example of an electrical circuit model according to an embodiment. Specifically, FIG. 6 illustrates an example of an equivalent electrical circuit model corresponding to the electrode placement of FIG. 5. The model includes the parallel resistances $R_{PR}$ and $R_{PL}$. The two resistances $R_{IN}$ are smaller than $R_{PL}$ and $R_{PR}$. Because current can pass through the peritoneal cavity, a change in intraperitoneal volume may be accurately measured. Before measuring the change in intraperitoneal volume, calibration may be performed with a volume of initial fresh dialysate.

Figure 7:
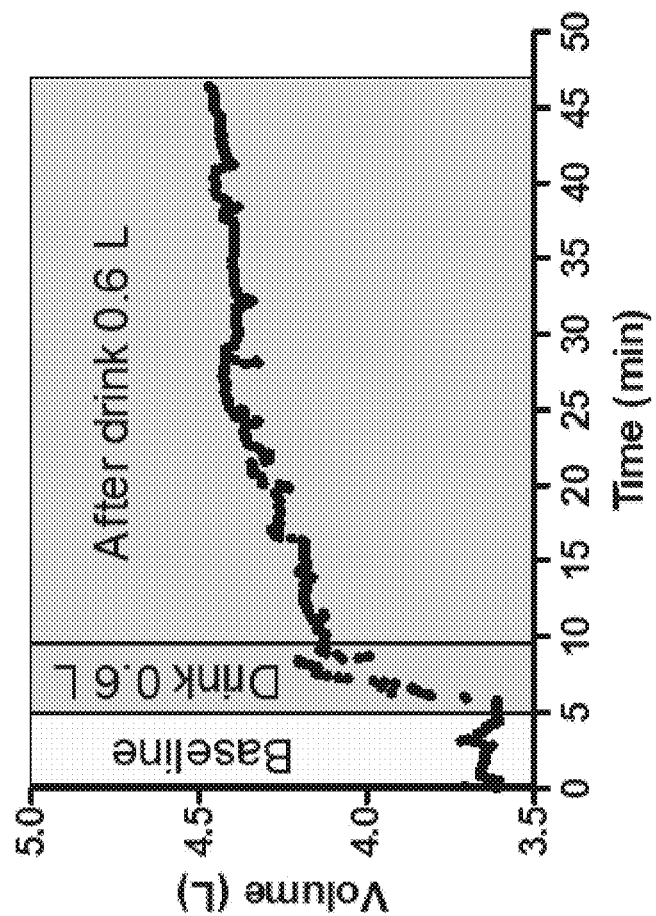
FIG. 7 illustrates an example of a chart of lower abdominal fluid volume over time according to an embodiment.

FIG. 7 illustrates an example of a chart of lower abdominal fluid volume over time according to an embodiment. Specifically, FIG. 7 illustrates a chart of measurements of lower abdominal fluid in a normal subject, using the model of FIG. 4. Four electrodes were placed on the subject, who was in a sitting position, in the configuration shown in FIG. 3. Measuring included three phases: (1) baseline in the first five minutes; (2) drinking 0.6 liters of water during the second five minutes; and (3) change in water in the bladder for 30 minutes thereafter. In this example, there was no fluid introduced to the peritoneal and other compartments, such as muscle mass and interstitial fluid. Therefore, the change in lower abdominal fluid may be considered a fluid increase in the bladder.

Figure 8:
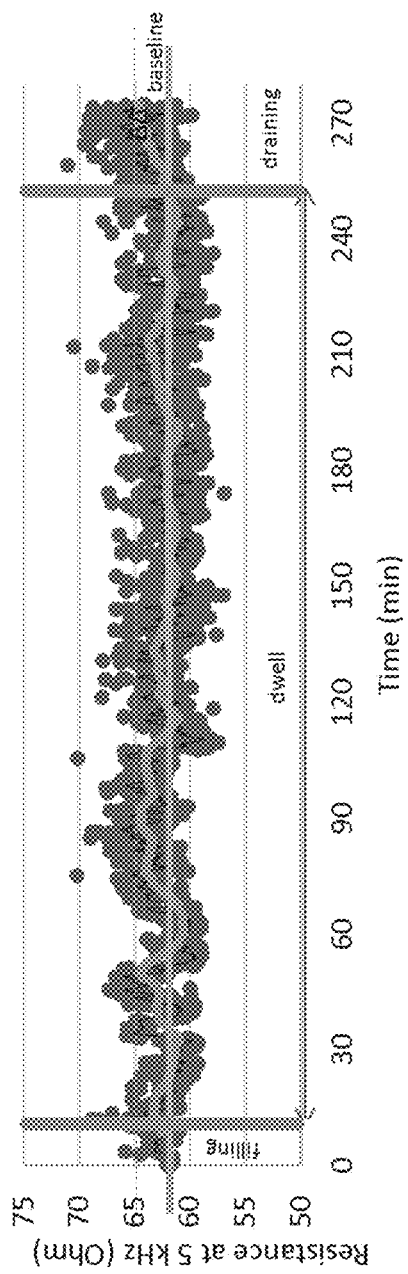
FIG. 8 illustrates an example of a chart of lower abdominal fluid volume over time according to an embodiment.

FIG. 8 illustrates an example of a chart of lower abdominal fluid volume over time according to an embodiment. Specifically, FIG. 8 illustrates a chart of measurements (i.e., change in resistance at 5 Hz) of lower abdominal fluid during dwell time in a peritoneal dialysis treatment, using the model of FIG. 4. Four electrodes were placed on the subject, in the configuration shown in FIG. 3. The procedure of the peritoneal dialysis treatment included three phases: (a) infusion of 2 liters of dialysate; (b) dwell time of four hours; and (3) drain phase. In FIG. 8, no change in fluid corresponding to infusion or drain phase can be observed, because the measurements were only in the interstitial compartment and not in the peritoneal cavity. The resistance measurements of FIG. 8 are likely to indicate change in fluid in the interstitial compartment.

Figure 9:
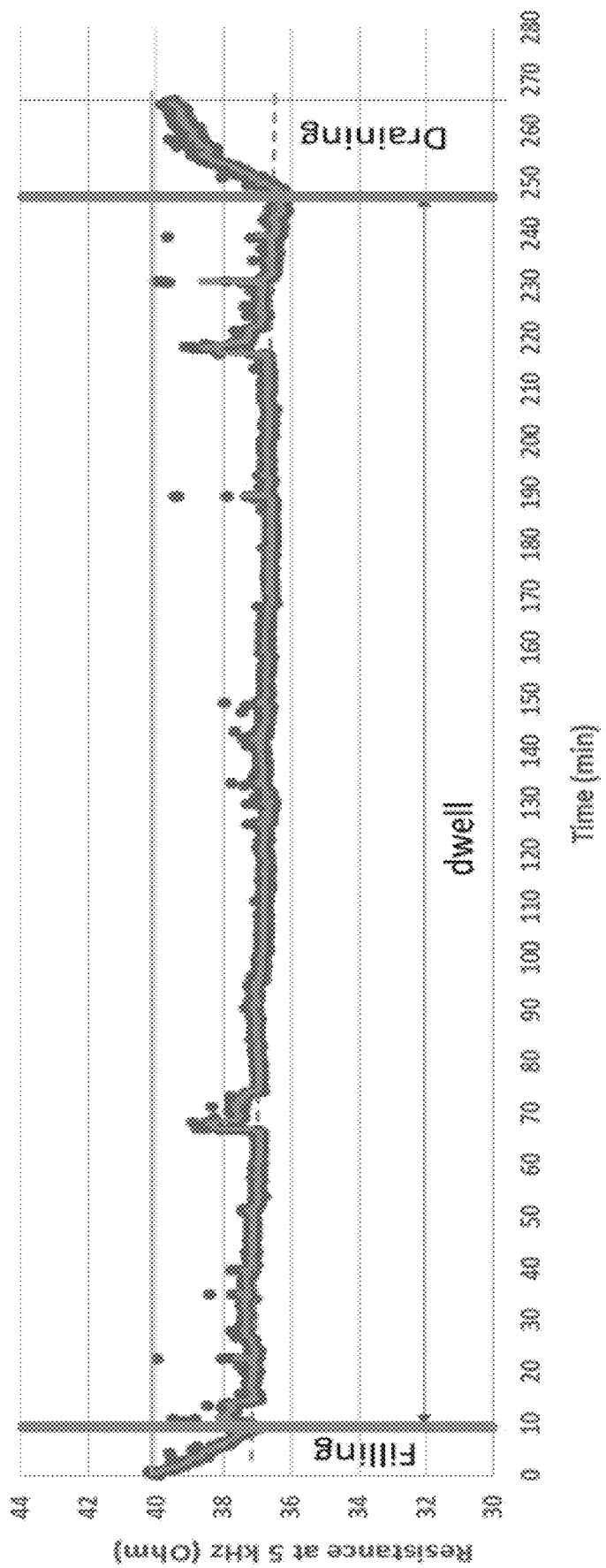
FIG. 9 illustrates an example of a chart of peritoneal volume over time according to an embodiment.

FIG. 9 illustrates an example of a chart of peritoneal volume over time according to an embodiment. Specifically, FIG. 9 illustrates a chart of monitoring of fluid change in the peritoneal cavity of a peritoneal dialysis patient, using the model of FIG. 6. Eight electrodes were placed on the subject, in the configuration shown in FIG. 5. In this example, three phases (i.e., infusion, dwell time, and draining) can be observed clearly, because the model allows for assessment of total changes in fluid volume.

Figure 12A:
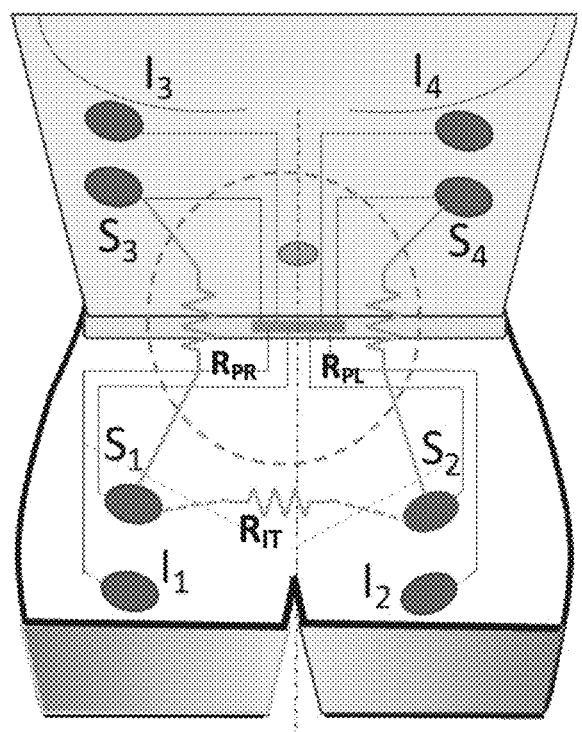
FIGS. 12A-12B illustrate an example of monitoring both intraperitoneal volume and extraperitoneal volume according to an embodiment.
Figure 12B:
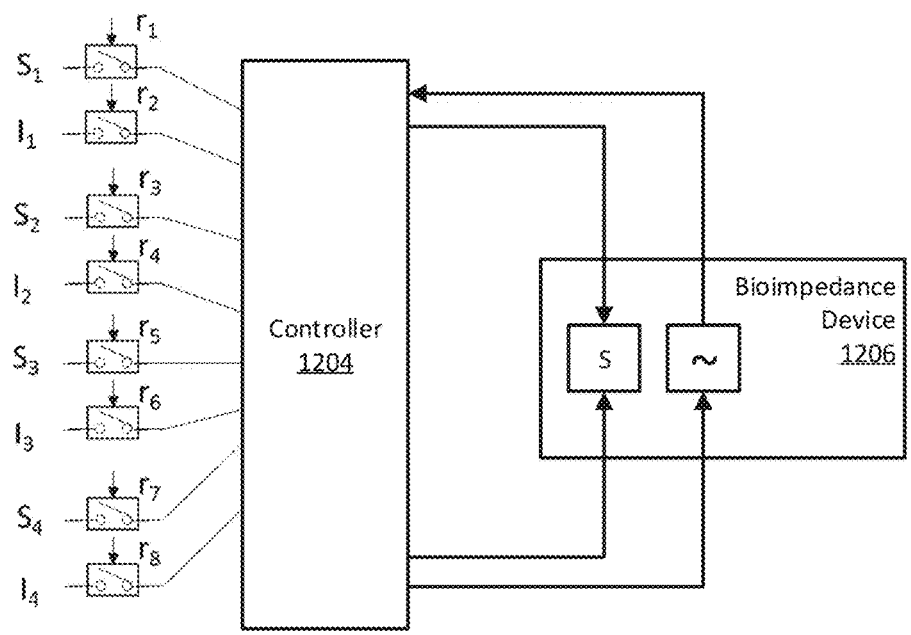

FIGS. 12A-12B illustrate an example of monitoring both intraperitoneal volume (EPV) and extraperitoneal volume (IPV) according to an embodiment. Measuring IPV using segmental bioimpedance is a powerful approach to evaluating the function of removing excess fluid via the peritoneal membrane during peritoneal dialysis. In addition, monitoring IPV during peritoneal dialysis treatment can allow for identification of the maximal ultrafiltration volume, thus allowing for optimization of dwell time for individual patients. However, if monitoring EPV assumes constant EPV in the surrounding area of the peritoneal cavity, then changes in the EPV may interfere with IPV measurements.

The following is an example of an approach to assessing EPV during peritoneal treatment, allowing for evaluation of the relationship between EPV and IPV during treatment. As discussed above, EPV may be assessed using four electrodes and IPV may be measured using eight electrodes. The example illustrated in FIGS. 12A-12B allows for continuously measuring both EPV and IPV, using a switch to selectively transmit the signals from eight electrodes to the two inputs of a bioimpedance device.

Specifically, FIG. 12A illustrates placements of eight electrodes I1, S1, I2, S2, I3, S3, I4, S4. Two electrodes I1, I3 on the patient's right side and two electrodes I2, I4 on the patient's left side are used to inject current. Two electrodes S1, S3 on the patient's right side and two electrodes S2, S4 on the patient's left side are used to measure voltage producing the resistances $R_{PR}$ and $R_{PL}$ on the patient's right and left sides, respectively. $R_{IT}$ represents resistance in the interstitial tissue.

As illustrated in FIG. 12B, EPV and IPV may be measured using one or more switches communicatively coupled with the electrodes. In this example, switching uses eight relay boxes ($r_1$ through $r_8$) for the eight electrodes illustrated in FIG. 12A. Connections between the electrodes and relay boxes may be wired, wireless, or a combination thereof. The relay boxes are configured to transfer signals from individual electrodes to input points of a bioimpedance device 1206. A controller 1204 may include one or more processors and may be configured to use the relay boxes to automatically and alternatively switch between the electrodes to measure IPV (by $R_{PR}$ and $R_{PL}$) and EPV (by $R_{IT}$). In an embodiment, the controller 1204 includes one or more settings that determine the sample rate(s) and/or interval(s) of measurement between IPV and EPV. The setting(s) may be adjustable, for example, via an application programming interface (API) and/or user interface (not shown in FIG. 12B).

3. Flow Diagram

Figure 10:
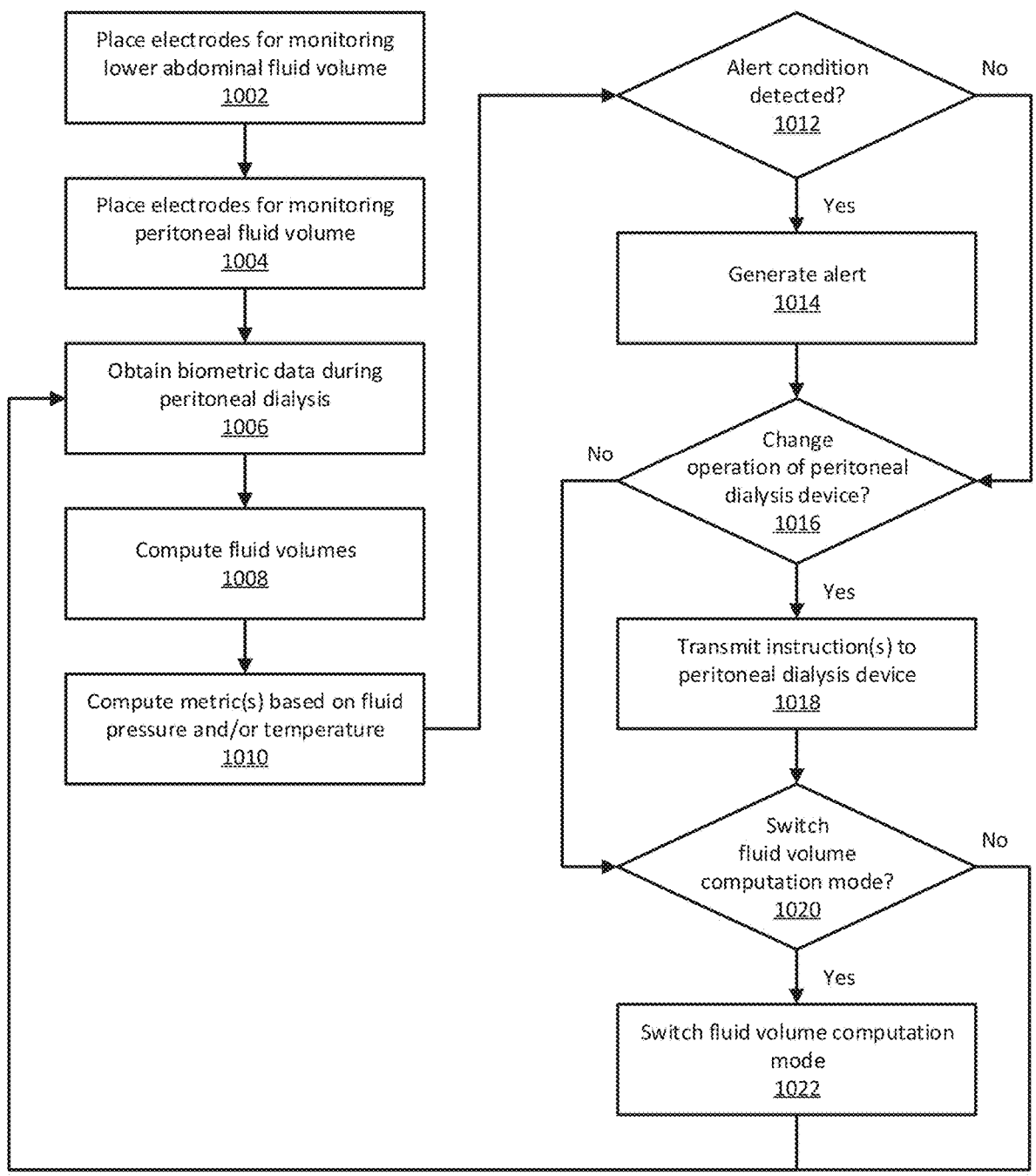
FIG. 10 is a flow diagram of an example of operations for monitoring volumes during peritoneal dialysis according to an embodiment.

FIG. 10 is a flow diagram of an example of operations for monitoring fluid volumes during peritoneal dialysis according to an embodiment. One or more operations illustrated in FIG. 10 may be modified, rearranged, or omitted all together. Accordingly, the particular sequence of operations illustrated in FIG. 10 should not be construed as limiting the scope of one or more embodiments.

In an embodiment, electrodes are placed on a patient for monitoring lower abdominal fluid volume (1002). The electrodes may be placed as illustrated in FIG. 3, as discussed above.

In an embodiment, electrodes are placed on a patient for monitoring peritoneal fluid volume (1004). The electrodes may include the electrodes illustrated in FIG. 5, as discussed above, which include the electrodes illustrated in FIG. 3 that may also be used to compute lower abdominal fluid volume.

In an embodiment, a monitoring device obtains biometric data during peritoneal dialysis (1006). The biometric data may include bioimpedance data from the electrodes, and may also include data corresponding to fluid pressure and/or fluid temperature. The monitoring device obtains the biometric data continuously, i.e., on an ongoing basis and/or at regular intervals, during peritoneal dialysis. As described above, the monitoring device may obtain some or all of the biometric data wirelessly.

In an embodiment, the monitoring device computes fluid volumes (1008). Specifically, the monitoring device computes lower abdominal fluid volumes (e.g., interstitial fluid volume and/or urinary bladder volume) and/or peritoneal fluid volumes. The monitoring device may include two or more computation modes for computing different types of fluid volumes and may be configured to switch between the computation modes, based on user input and/or an automated switching condition. Alternatively, the monitoring device may be configured to compute two or more kinds of fluid volumes in parallel, i.e., without needing to switch between computation modes.

In an embodiment, the monitoring device computes one or more metrics based on fluid pressure and/or fluid temperature (1010). A metric may be based on a combination of fluid pressure, fluid temperature, and/or one or more fluid volumes. For example, the monitoring device may compute tissue compliance as a function of change in fluid pressure and change in fluid volume (e.g., dP/dV).

In an embodiment, the monitoring device determines whether an alert condition is detected (1012). An alert condition is a condition that requires human attention. For example, an alert condition may indicate a rapid change in fluid volume, fluid volume above or below a threshold value, a rapid change in tissue compliance, or tissue compliance above or below a threshold value. Because the monitoring device computes fluid volumes and/or other metrics continuously, one or more embodiments are capable of detecting alert conditions promptly, without undue delay that could compromise a patient's health or care thereof. If the monitoring device detects an alert condition, then the monitoring device generates an alert (1014) indicating the alert condition. The monitoring device may transmit the alert, for example, to a user interface of the monitoring device.

In an embodiment, the monitoring device determines whether to change operation of a peritoneal dialysis device (1016). For example, the monitoring device may detect a peak in ultrafiltration volume. In general, the monitoring device may detect a condition that warrants a change in state of a switch, pump, and/or another component of the peritoneal dialysis device. If the corresponding condition(s) is/are met, the monitoring device transmits one or more instructions to the peritoneal dialysis device (1018), instructing the peritoneal dialysis device (or a component thereof) to change its operation accordingly. Alternatively, the monitoring device may generate an alert instructing a human to manually adjust operation of the peritoneal dialysis device.

In an embodiment, the monitoring device determines whether to switch fluid volume computation mode (1020). Specifically, the monitoring device may determine, based on user input and/or an automated switching condition, that it should switch from one computation mode to another. If the corresponding condition(s) is/are met, then the monitoring device switches fluid volume computation modes (1022). For example, the monitoring device may switch from computing lower abdominal fluid volume to computing peritoneal fluid volume, or vice versa.

As described above, the monitoring device is configured to monitor fluid volumes continuously. Accordingly, the monitoring device continues to obtain biometric data and perform computations based on the biometric data until a terminating condition (not shown) is met. For example, the continuous monitoring may terminate when the peritoneal dialysis treatment is complete, when the monitoring device is powered down, responsive to user input, and/or responsive an automated termination condition. If the monitoring device switches between computation modes, then the term "continuously," as used herein, applies to the period of time during which the monitoring device is in the corresponding computation mode.

4. Miscellaneous

In an embodiment, a system includes one or more devices, including one or more hardware processors, that are configured to perform any of the operations described herein and/or recited in any of the claims.

In an embodiment, one or more non-transitory computer-readable storage media store(s) instructions that, when executed by one or more hardware processors, cause performance of any of the operations described herein and/or recited in any of the claims.

Any combination of the features and functionalities described herein may be used in accordance with an embodiment. In the foregoing specification, embodiments have been described with reference to numerous specific details that may vary from implementation to implementation. Accordingly, the specification and figures are to be regarded in an illustrative rather than a restrictive sense. The sole and exclusive indicator of the scope of the invention, and what is intended by the Applicant to be the scope of the invention, is the literal and equivalent scope of the set of claims that issue from this application, in the specific form in which such claims issue, including any subsequent correction.

5. Computing Devices

In an embodiment, techniques described herein are implemented by one or more special-purpose computing devices (i.e., computing devices specially configured to perform certain functionality). The special-purpose computing device(s) may be hard-wired to perform the techniques and/or may include digital electronic devices such as one or more application-specific integrated circuits (ASICs), field programmable gate arrays (FPGAs), and/or network processing units (NPUs) that are persistently programmed to perform the techniques. Alternatively or additionally, a computing device may include one or more general-purpose hardware processors programmed to perform the techniques pursuant to program instructions in firmware, memory, and/or other storage. Alternatively or additionally, a special-purpose computing device may combine custom hard-wired logic, ASICs, FPGAs, or NPUs with custom programming to accomplish the techniques. A special-purpose computing device may include a desktop computer system, portable computer system, handheld device, networking device, and/or any other device(s) incorporating hard-wired and/or program logic to implement the techniques.

Figure 11:
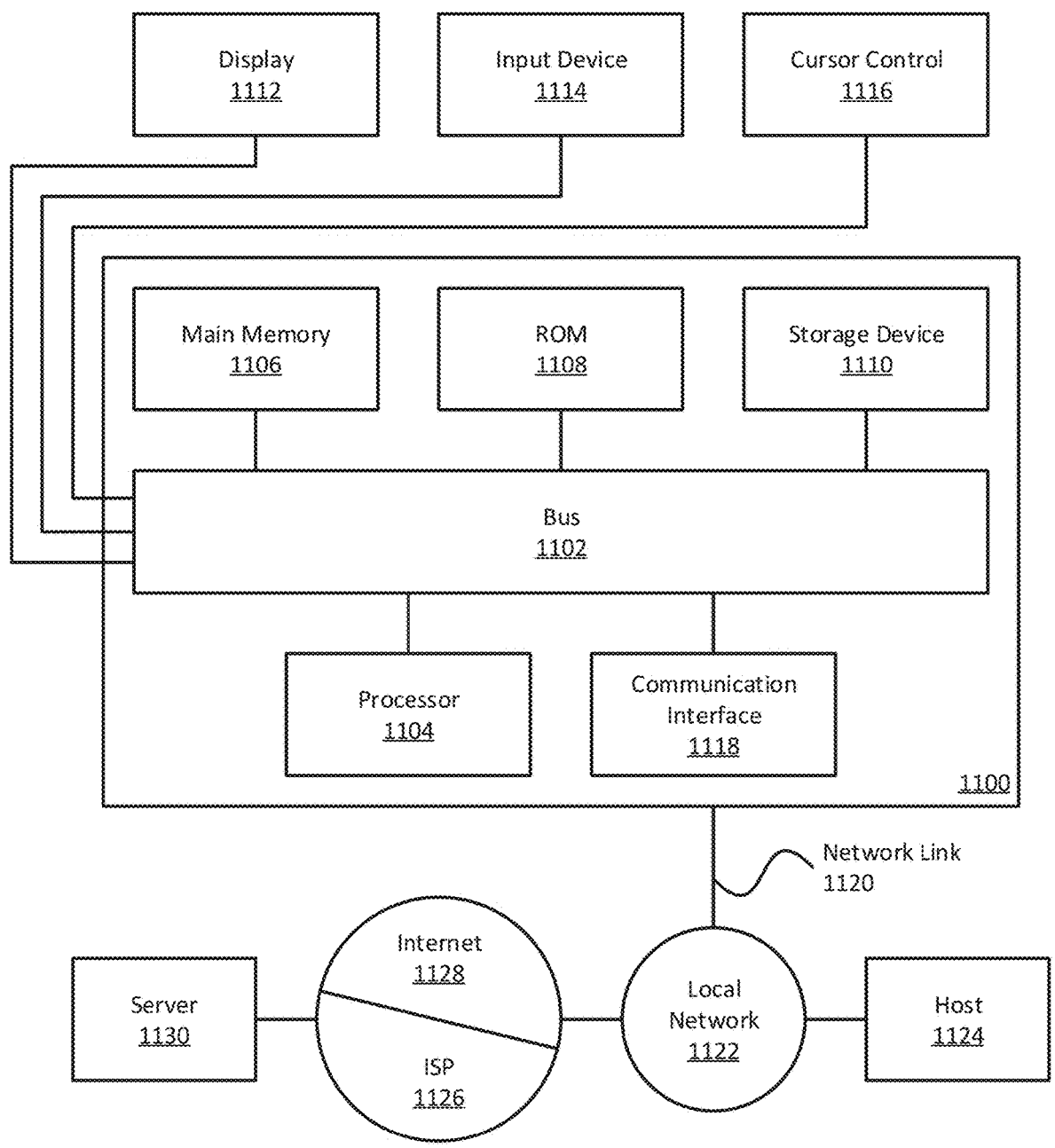
FIG. 11 is a block diagram of an example of a computer system according to an embodiment.

For example, FIG. 11 is a block diagram of an example of a computer system 1100 according to an embodiment. Computer system 1100 includes a bus 1102 or other communication mechanism for communicating information, and a hardware processor 1104 coupled with the bus 1102 for processing information. Hardware processor 1104 may be a general-purpose microprocessor.

Computer system 1100 also includes a main memory 1106, such as a random access memory (RAM) or other dynamic storage device, coupled to bus 1102 for storing information and instructions to be executed by processor 1104. Main memory 1106 also may be used for storing temporary variables or other intermediate information during execution of instructions to be executed by processor 1104. Such instructions, when stored in one or more non-transitory storage media accessible to processor 1104, render computer system 1100 into a special-purpose machine that is customized to perform the operations specified in the instructions.

Computer system 1100 further includes a read only memory (ROM) 1108 or other static storage device coupled to bus 1102 for storing static information and instructions for processor 1104. A storage device 1110, such as a magnetic disk or optical disk, is provided and coupled to bus 1102 for storing information and instructions.

Computer system 1100 may be coupled via bus 1102 to a display 1112, such as a liquid crystal display (LCD), plasma display, electronic ink display, cathode ray tube (CRT) monitor, or any other kind of device for displaying information to a computer user. An input device 1114, including alphanumeric and other keys, may be coupled to bus 1102 for communicating information and command selections to processor 1104. Alternatively or additionally, computer system 1100 may receive user input via a cursor control 1116, such as a mouse, a trackball, a trackpad, or cursor direction keys for communicating direction information and command selections to processor 1104 and for controlling cursor movement on display 1112. This input device typically has two degrees of freedom in two axes, a first axis (e.g., x) and a second axis (e.g., y), that allows the device to specify positions in a plane. Alternatively or additionally, computer system 11 may include a touchscreen. Display 1112 may be configured to receive user input via one or more pressure-sensitive sensors, multi-touch sensors, and/or gesture sensors. Alternatively or additionally, computer system 1100 may receive user input via a microphone, video camera, and/or some other kind of user input device (not shown).

Computer system 1100 may implement the techniques described herein using customized hard-wired logic, one or more ASICs or FPGAs, firmware, and/or program logic which in combination with other components of computer system 1100 causes or programs computer system 1100 to be a special-purpose machine. According to one embodiment, the techniques herein are performed by computer system 1100 in response to processor 1104 executing one or more sequences of one or more instructions contained in main memory 1106. Such instructions may be read into main memory 1106 from another storage medium, such as storage device 1110. Execution of the sequences of instructions contained in main memory 1106 causes processor 1104 to perform the process steps described herein. Alternatively or additionally, hard-wired circuitry may be used in place of or in combination with software instructions.

The term "storage media" as used herein refers to one or more non-transitory media storing data and/or instructions that cause a machine to operate in a specific fashion. Such storage media may comprise non-volatile media and/or volatile media. Non-volatile media includes, for example, optical or magnetic disks, such as storage device 1110. Volatile media includes dynamic memory, such as main memory 1106. Common forms of storage media include, for example, a floppy disk, a flexible disk, hard disk, solid state drive, magnetic tape or other magnetic data storage medium, a CD-ROM or any other optical data storage medium, any physical medium with patterns of holes, a RAM, a programmable read-only memory (PROM), an erasable PROM (EPROM), a FLASH-EPROM, non-volatile random-access memory (NVRAM), any other memory chip or cartridge, content-addressable memory (CAM), and ternary content-addressable memory (TCAM).

A storage medium is distinct from but may be used in conjunction with a transmission medium. Transmission media participate in transferring information between storage media. Examples of transmission media include coaxial cables, copper wire, and fiber optics, including the wires that comprise bus 1102. Transmission media may also take the form of acoustic or light waves, such as those generated during radio-wave and infra-red data communications.

Various forms of media may be involved in carrying one or more sequences of one or more instructions to processor 1104 for execution. For example, the instructions may initially be carried on a magnetic disk or solid state drive of a remote computer. The remote computer may load the instructions into its dynamic memory and send the instructions over a network, via a network interface controller (NIC), such as an Ethernet controller or Wi-Fi controller. A NIC local to computer system 1100 may receive the data from the network and place the data on bus 1102. Bus 1102 carries the data to main memory 1106, from which processor 1104 retrieves and executes the instructions. The instructions received by main memory 1106 may optionally be stored on storage device 1110 either before or after execution by processor 1104.

Computer system 1100 also includes a communication interface 1118 coupled to bus 1102. Communication interface 1118 provides a two-way data communication coupling to a network link 1120 that is connected to a local network 1122. For example, communication interface 1118 may be an integrated services digital network (ISDN) card, cable modem, satellite modem, or a modem to provide a data communication connection to a corresponding type of telephone line. As another example, communication interface 1118 may be a local area network (LAN) card to provide a data communication connection to a compatible LAN. Wireless links may also be implemented. In any such implementation, communication interface 1118 sends and receives electrical, electromagnetic or optical signals that carry digital data streams representing various types of information.

Network link 1120 typically provides data communication through one or more networks to other data devices. For example, network link 1120 may provide a connection through local network 1122 to a host computer 1124 or to data equipment operated by an Internet Service Provider (ISP) 1126. ISP 1126 in turn provides data communication services through the world wide packet data communication network now commonly referred to as the "Internet" 1128. Local network 1122 and Internet 1128 both use electrical, electromagnetic or optical signals that carry digital data streams. The signals through the various networks and the signals on network link 1120 and through communication interface 1118, which carry the digital data to and from computer system 1100, are example forms of transmission media.

Computer system 1100 can send messages and receive data, including program code, through the network(s), network link 1120 and communication interface 1118. In the Internet example, a server 1130 might transmit a requested code for an application program through Internet 1128, ISP 1126, local network 1122, and communication interface 1118.

The received code may be executed by processor 1104 as it is received, and/or stored in storage device 1110, or other non-volatile storage for later execution.

What is claimed is:

1. One or more non-transitory computer-readable media storing instructions that, when executed by one or more processors, cause the one or more processors to perform operations comprising:

computing a plurality of lower abdominal fluid volumes, continuously during a dwell time of a peritoneal dialysis treatment, based at least on bioimpedance data from a first plurality of electrodes positioned on a patient's upper thighs;

computing a plurality of intraperitoneal volumes, continuously during the dwell time of the peritoneal dialysis treatment, based at least on the bioimpedance data from the first plurality of electrodes and bioimpedance data from a second plurality of electrodes positioned on the patient's torso; and controlling operation of a pump of a peritoneal dialysis device to maximize ultrafiltration volume, based at least on one or more of the plurality of lower abdominal fluid volumes and one or more of the plurality of intraperitoneal volumes, wherein computing the peritoneal volumes comprises applying bioimpedance data from the first plurality of electrodes to an electrical circuit model that is based at least in part on (a) a first resistance between a first electrode in the first plurality of electrodes and a second electrode in the second plurality of electrodes in parallel with (b) a second resistance between a third electrode in the first plurality of electrodes and a fourth electrode in the second plurality of electrodes.

2. The one or more non-transitory computer-readable media of claim 1, the operations further comprising:

detecting a first switching condition for switching from a first computation mode for computing the plurality of lower abdominal fluid volumes to a second computation mode for computing the plurality of intraperitoneal volumes; and responsive to detecting the first switching condition, switching from the first computation mode to the second computation mode.

3. The one or more non-transitory computer-readable media of claim 2, the operations further comprising:

detecting a second switching condition for switching from the second computation mode to the first computation mode; and responsive to detecting the second switching condition, switching from the second computation mode to the first computation mode.

4. The one or more non-transitory computer-readable media of claim 1, the operations further comprising:

detecting a first switching condition for switching from a first computation mode for computing the plurality of intraperitoneal volumes to a second computation mode for computing the plurality of lower abdominal fluid volumes; and responsive to detecting the first switching condition, switching from the first computation mode to the second computation mode.

5. The one or more non-transitory computer-readable media of claim 1, wherein the first plurality of electrodes comprises a first pair of electrodes in close proximity on the patient's upper right thigh and a second pair of electrodes in close proximity on the patient's upper left thigh, and wherein the second plurality of electrodes comprises a third pair of electrodes in close proximity on the patient's right torso and a fourth pair of electrodes in close proximity on the patient's left torso.

6. The one or more non-transitory computer-readable media of claim 1, the operations further comprising:

transmitting an instruction to control operation of a peritoneal dialysis device, based at least on one or more of the plurality of lower abdominal fluid volumes and/or the plurality of intraperitoneal volumes.

7. The one or more non-transitory computer-readable media of claim 1, wherein at least the first plurality of electrodes is integrated into a garment worn by the patient.

8. The one or more non-transitory computer-readable media of claim 1, wherein the plurality of lower abdominal fluid volumes correspond to one or more of bladder volumes or interstitial volumes.

9. One or more non-transitory computer-readable media storing instructions that, when executed by one or more processors, cause the one or more processors to perform operations comprising:

computing a plurality of lower abdominal fluid volumes, continuously during a dwell time of a peritoneal dialysis treatment, based at least on bioimpedance data from a first plurality of electrodes positioned on a patient's upper thighs;

computing a plurality of intraperitoneal volumes, continuously during the dwell time of the peritoneal dialysis treatment, based at least on the bioimpedance data from the first plurality of electrodes and bioimpedance data from a second plurality of electrodes positioned on the patient's torso; and controlling operation of a pump of a peritoneal dialysis device to maximize ultrafiltration volume, based at least on one or more of the plurality of lower abdominal fluid volumes and one or more of the plurality of intraperitoneal volumes, wherein computing the plurality of lower abdominal fluid volumes comprises applying bioimpedance data from the first plurality of electrodes to an electrical circuit model that is based at least in part on interstitial tissue resistance and peritoneal cavity resistance.

10. The one or more non-transitory computer-readable media of claim 9, wherein the electrical circuit model includes at least interstitial tissue resistance, peritoneal cavity resistance, local muscle resistance, and urinary bladder resistance in parallel, wherein the electrical circuit model can be simplified as interstitial tissue resistance and peritoneal cavity resistance in parallel, and wherein interstitial tissue resistance is greater than peritoneal cavity resistance, such that the electrical model can be used to compute changes in lower abdominal fluid volume.

* * * * *

UNITED STATES PATENT AND TRADEMARK OFFICE
CERTIFICATE OF CORRECTION

| | | |
|---|---|---|
| PATENT NO. | : 12,076,472 B2 | Page 1 of 1 |
| APPLICATION NO. | : 17/066554 | |
| DATED | : September 3, 2024 | |
| INVENTOR(S) | : Peter Kotanko et al. | |

It is certified that error appears in the above-identified patent and that said Letters Patent is hereby corrected as shown below:

In the Specification

Column 13, Line 40, delete "Hz" and insert -- kHz --

Signed and Sealed this
First Day of October, 2024

*Katherine Kelly Vidal*

Katherine Kelly Vidal
*Director of the United States Patent and Trademark Office*